US010869968B2

(12) United States Patent
Meier (10) Patent No.: US 10,869,968 B2
(45) Date of Patent: Dec. 22, 2020

(54) DRUG DELIVERY DEVICE AND RETAINING MEMBER FOR A DRUG DELIVERY DEVICE

(71) Applicant: SANOFI-AVENTIS DEUTSCHLAND GMBH, Frankfurt am Main (DE)

(72) Inventor: Alex Meier, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 116 days.

(21) Appl. No.: 15/567,212

(22) PCT Filed: Apr. 20, 2016

(86) PCT No.: PCT/EP2016/058688
§ 371 (c)(1),
(2) Date: Oct. 17, 2017

(87) PCT Pub. No.: WO2016/169946
PCT Pub. Date: Oct. 27, 2016

(65) Prior Publication Data
US 2018/0126087 A1 May 10, 2018

(30) Foreign Application Priority Data
Apr. 23, 2015 (EP) .................... 15164815

(51) Int. Cl.
*A61M 5/315* (2006.01)
*A61M 5/50* (2006.01)
(52) U.S. Cl.
CPC .... *A61M 5/31576* (2013.01); *A61M 5/31551* (2013.01); *A61M 5/5066* (2013.01)

(58) Field of Classification Search
CPC ........ A61M 5/5066; A61M 2005/5073; A61M 5/5086; A61M 5/31576; A61M 5/50;
(Continued)

(56) References Cited

U.S. PATENT DOCUMENTS

| 4,226,235 A | 10/1980 | Sarnoff et al. |
| 4,246,898 A | 1/1981 | Travalent et al. |

(Continued)

FOREIGN PATENT DOCUMENTS

| CN | 201862083 | 6/2011 |
| EP | 0327910 | 8/1989 |

(Continued)

OTHER PUBLICATIONS

International Search Report and Written Opinion in International Application No. PCT/US2016/058688, dated Jun. 27, 2016, 9 pages.

(Continued)

*Primary Examiner* — Nathan R Price
*Assistant Examiner* — Melissa A Snyder
(74) *Attorney, Agent, or Firm* — Fish & Richardson P.C.

(57) ABSTRACT

A drug delivery device includes a housing, a mechanical assembly which is at least partially accommodated in the housing and a retaining member for retaining the mechanical assembly in the housing wherein the retaining member is engaged with the housing such that the device is configured to be damaged when the mechanical assembly or parts thereof are forcefully separated from the housing.

17 Claims, 3 Drawing Sheets

(58) Field of Classification Search
CPC ............ A61M 5/321; A61M 2205/273; A61M 2005/31506; A61M 5/31551
See application file for complete search history.

(56) References Cited

U.S. PATENT DOCUMENTS

| | | | | |
|---|---|---|---|---|
| 5,584,815 | A * | 12/1996 | Pawelka | A61M 5/19 604/135 |
| 2002/0007142 | A1* | 1/2002 | Hjertman | A61M 5/30 604/38 |
| 2002/0032412 | A1* | 3/2002 | Riemelmoser | A61M 5/326 604/197 |
| 2008/0045899 | A1* | 2/2008 | Wu | A61M 5/322 604/110 |
| 2009/0254043 | A1* | 10/2009 | Van Bulow | A61M 5/24 604/207 |

FOREIGN PATENT DOCUMENTS

| | | |
|---|---|---|
| EP | 1935444 | 6/2008 |
| JP | S55-122562 | 9/1980 |
| JP | H1-24838 | 1/1990 |
| JP | 2012-509736 | 4/2012 |
| WO | WO 2014/108551 | 7/2014 |
| WO | WO 2014/121929 | 8/2014 |

OTHER PUBLICATIONS

International Preliminary Report on Patentability in International Application No. PCT/US2016/058688, dated Oct. 24, 2017, 7 pages.

\* cited by examiner

DRUG DELIVERY DEVICE AND RETAINING MEMBER FOR A DRUG DELIVERY DEVICE

CROSS REFERENCE TO RELATED APPLICATIONS

The present application is the national stage entry of International Patent Application No. PCT/EP2016/058688, filed on Apr. 20, 2016, and claims priority to Application No. EP 15164815.1, filed in on Apr. 23, 2015, the disclosures of which are expressly incorporated herein in entirety by reference thereto.

TECHNICAL FIELD

The present disclosure relates to a drug delivery device, for example, an injection device.

BACKGROUND

Although the drug delivery device may not be meant to be refilled, manipulated devices have come on the market. Often, the refilled drug in such a manipulated device is not identical to the drug originally contained in the device. As an example, the refilled drug in the manipulated device may be a diluted form of the original drug. The diluted drug may be non-discernable for a user from the original drug, which may pose a considerable health risk to the user.

SUMMARY

The present disclosure provides in certain aspects a drug delivery device having improved properties.

The drug delivery device is preferably a disposable device configured to be disposed when a drug reservoir is empty. Such a drug delivery device may also be referred to as a non-refillable or non-reusable device as the device may not be configured to be refilled and/or reused with a refilled drug. Refilling may mean exchanging an empty drug reservoir with a drug reservoir containing a drug or may mean refilling an empty drug reservoir with a drug.

According to a first aspect of the present disclosure, a drug delivery device comprises a housing, a mechanical assembly which is at least partially accommodated in the housing and a retaining member for retaining the mechanical assembly in the housing. In particular, the retaining member secures the mechanical assembly to the housing such that it remains at least partially accommodated in the housing. The drug delivery device may comprise a piston rod.

The mechanical assembly may be configured to drive the piston rod forwards for dispensing a dose of a drug. During the use of the device, in particular in a dispense operation, the piston rod and/or parts of the mechanical assembly may move from a start position towards an end position in the device. The start position may be a most proximal position of the respective member relative to the housing. Furthermore, the mechanical assembly may be configured to set a size of a dose to be dispensed. Setting the dose may comprise selecting the size of a dose and/or preparing the mechanical assembly for a dispense operation.

The drug delivery device may be an injection device, in particular a pen-type injection device. The device may comprise a drug reservoir, in particular a cartridge. The drug reservoir may be configured to be mounted at a distal end of the housing. The term "distal end" may describe an end of the device or a part thereof which is closest to a dispensing end of the device. The term "proximal end" may describe an end of the device or a part thereof which is furthest away from the dispensing end of the device. Analogously, the term "distal direction" may describe a direction towards a dispensing end of the device and the term "proximal direction" may describe a direction away from the dispensing end of the device.

The drug delivery device may be a non-reusable device. As an example, the device may be configured for not supporting a dismounting of a drug reservoir. The drug reservoir may only be forcefully dismounted from the housing. A reuse of the device may further require a reset of the mechanical assembly and/or a piston rod to a start position in the device. The drug delivery device may be configured for not supporting such a reset. For example, the drug delivery device may be configured for not supporting a removal of the mechanical assembly from the housing which may be required for resetting the device. However, although the device may not be configured and intended to be reused, a user may try to forcefully disassemble the device, refill the drug and reset components of the device to their respective start positions.

According to the present disclosure, the retaining member is engaged with the housing such that the device is configured to be damaged when the mechanical assembly or parts thereof are forcefully separated from the housing. A damage of the device may comprise a damage of the mechanical assembly, in particular of a component engaged with the retaining member when the mechanical assembly is retained in the housing. Additionally or alternatively, the retaining member, the housing or other parts of the device may be damaged during such a forceful disassembly.

A damage of a component may comprise a permanent deformation, a crack being generated in the component and/or a partial or complete breakage of the component. Preferably, the damage is permanent and visible such a manipulation of the device is detectable. The damage may prevent a reuse of the device, in particular a reuse of the device once the mechanical assembly or parts thereof have been disassembled from the housing. In particular, the damage may disable a proper functioning of the mechanical assembly and/or may disable correctly re-assembling the device.

The mechanical assembly may be configured to partially protrude out of the housing during normal use of the device, in particular during dose set and/or dose dispense operations. Accordingly, the mechanical assembly may be accessible for a user from outside. When trying to disassemble the mechanical assembly from the housing, the mechanical assembly may be gripped by a user and forcefully drawn completely out of the housing. Large bending and/or axial forces may have to be applied to draw the mechanical assembly completely out of the housing. In particular, a component of the mechanical assembly engaged with the retaining member may protrude out of the housing and may be gripped by a user when trying to manipulate the device.

The retaining member may be threadedly engaged with the mechanical assembly, in particular with a component of the mechanical assembly. The retaining member may comprise an inner thread for engagement with an outer thread of the mechanical assembly, in particular an outer thread of the component. The component of the mechanical assembly which is engaged with the retaining member may be configured as an indicator member for displaying information to the user. In particular, the indicator member may be configured to display the size of a dose of a drug to be dispensed. The indicator member may comprise indications, in particular numbers. An indication indicating the size of a set dose or other information related to the current status of the device may be visible in a dose display, in particular through an opening in the housing.

The retaining member may comprise a first engagement device and the housing may comprise a second engagement device, wherein the first and second engagement devices engage with each other. In particular, the retaining member is secured to the housing by the engagement of the devices. Preferably, the retaining member is fixed to the housing such that axial and rotational movements are prevented.

The first engagement device may comprise a projection. The second engagement device may comprise a recess for engagement with the projection. Alternatively, the first engagement device may comprise a recess and the second engagement device may comprise a projection. As an example, the first engagement device may comprise a ridge. The second engagement device may comprise a groove. The engagement devices may be configured for a tongue-and-groove connection.

The first engagement device may extend along a circumference of the retaining member, in particular along an outer circumference of the retaining member. The second engagement device may extend along a circumference of the housing, in particular along an inner circumference of the housing. The first and/or second engagement device may extend perpendicular to a longitudinal axis of the retaining member and/or the housing. Preferably, the engagement device covers a large part of the circumference. As an example, the engagement device may cover at least half of the circumference of the retaining member or housing, respectively. The engagement device may cover the entire circumference. In this case, the engagement device may be a closed ridge or groove, for example. By a large extension of the engagement devices, a large strength of connection between the retaining member and the housing may be achieved. Thereby, a disassembly is hampered. In particular, a large force may be required for disassembling the mechanical assembly from the housing which may result in a damage of the device during manipulation.

In an embodiment, the first and/or second engagement device comprises several separate parts. The separate parts may be located at different angular positions around a longitudinal axis of the retaining member and/or housing. Accordingly, the first and/or second engagement device may be interrupted. As an example, the engagement device may not extend along a part of the retaining member and/or housing which has a reduced thickness of material, in order to avoid an additional mechanical weakening of the retaining member and/or the housing. As a further example, the engagement member may be interrupted by an opening in the retaining member and/or the housing.

In an embodiment, an angular range of the circumference which is not covered by the respective device is smaller than 120°. The angular range not covered by the respective device may be an angular range of a coherent part of the circumference or may be the sum of angular ranges of separate parts not covered by engagement device. Accordingly, the angular range of the circumference covered by the respective device is at least 240°. The angular range may be an angular range of a coherent part of the circumference or may be the sum of angular ranges of separate parts. Accordingly, the engagement between the retaining member and the housing may be present in a large angular range of the circumference, in particular in a range larger than 240°, such that a large connection strength may be achieved.

In an embodiment, the device may be configured such that the connection strength of the retaining member with the housing is larger than the connection strength of the retaining member with the mechanical assembly. In other words, the force required for disengaging the retaining member from the housing may be larger than the force required for disengaging the retaining member from the mechanical assembly. The force may be purely axial force or may comprise a bending force.

Accordingly, when the mechanical assembly or parts thereof are forcefully separated from the housing, the retaining member may become disengaged from the mechanical assembly. In particular, the engagement of the retaining member with a component of the mechanical assembly, in particular a threaded engagement, may be lost. The engagement of the retaining member with the housing may be maintained. In particular, the retaining member may remain in the housing when the mechanical assembly or parts thereof are forcefully separated from the housing. The forceful disengagement of the retaining member from the mechanical assembly may lead to a damage of the mechanical assembly and/or the retaining member. Furthermore, such a disengagement may hamper or prevent a reassembly of the mechanical assembly with the housing. As an example, the device may be configured such that for assembling the device, the mechanical assembly has to be engaged with the retaining member before the mechanical assembly is assembled with the housing. When the retaining member remains in the housing during a forceful disassembly of the mechanical assembly, an engagement of the retaining member with the mechanical assembly may not be possible.

According to a further aspect of the present disclosure, a retaining member for retaining a mechanical assembly in a housing of a drug delivery device comprises a first engagement device for engagement with a second engagement device of the housing. The retaining member may comprise any structural and functional characteristics as the retaining member disclosed above. The first engagement device covers at least half of the circumference of the retaining member. Thereby, a strong connection force of the retaining member with the housing may be achieved and the manipulation of the device may be prevented.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

DETAILED DESCRIPTION

Like elements, elements of the same kind and identically acting elements may be provided with the same reference numerals in the figures.

Figure 1:
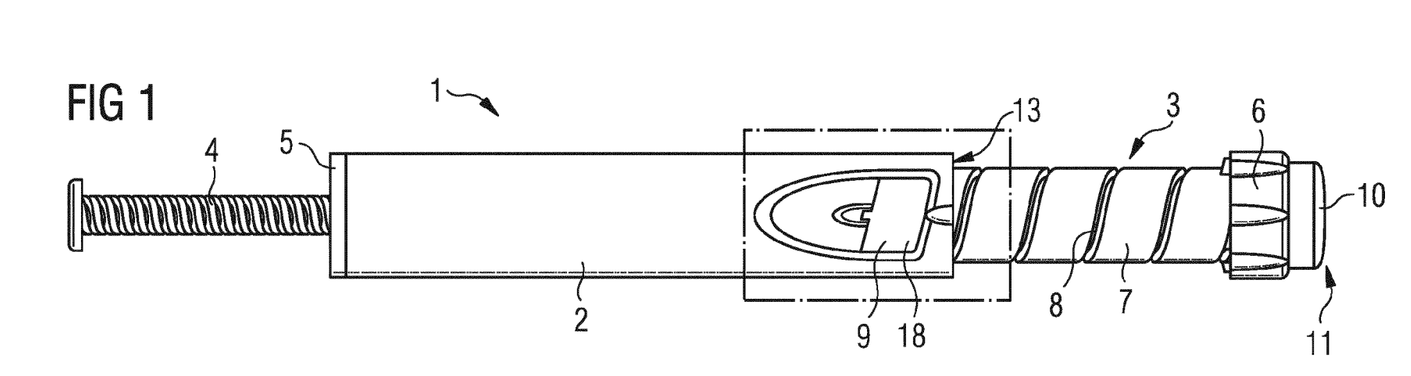
FIG. 1 shows a side view of a drug delivery device in an assembled state.

FIG. 1 shows a drug delivery device 1. The drug delivery device 1 is an injection device, in particular a pen-type injection device.

The drug delivery device 1 is a variable dose device such that a user can select the size of a dose. Alternatively, the drug delivery device 1 may be a fixed-dose device, i.e., a device wherein the size of a dose is fixed such that a user cannot select the size of the dose. The drug delivery device 1 may be configured for multiple dose applications. In this case the user may dispense multiple doses from the device, i.e. use the device in several dose dispense operations.

The drug delivery device 1 comprises a housing 2, in which a mechanical assembly 3 is partially accommodated. The mechanical assembly 3 may be configured to drive a piston rod 4 forwards for expelling a drug from a drug reservoir (not shown). The piston rod 4 may be configured as a lead screw. The piston rod 4 may be threadedly connected with the housing 2, for example by a part fixed to the housing 2. The drug may comprise insulin. The drug reservoir may be mounted to a distal end 5 of the housing 2. The drug reservoir may be configured as a cartridge. The cartridge may be accommodated in a cartridge holder. The drug reservoir may comprise a bung which is configured to be moved forwards by the piston rod 4.

The mechanical assembly 3 comprises an indicator member 7 for displaying information about the status of the device 1, in particular the size of a set dose. On its outer surface, the indicator member 7 comprises indications (not shown here), for example numbers, for indicating the size of the set dose. A dose setting member 6 is fixed to the indicator member 7.

Figure 2:
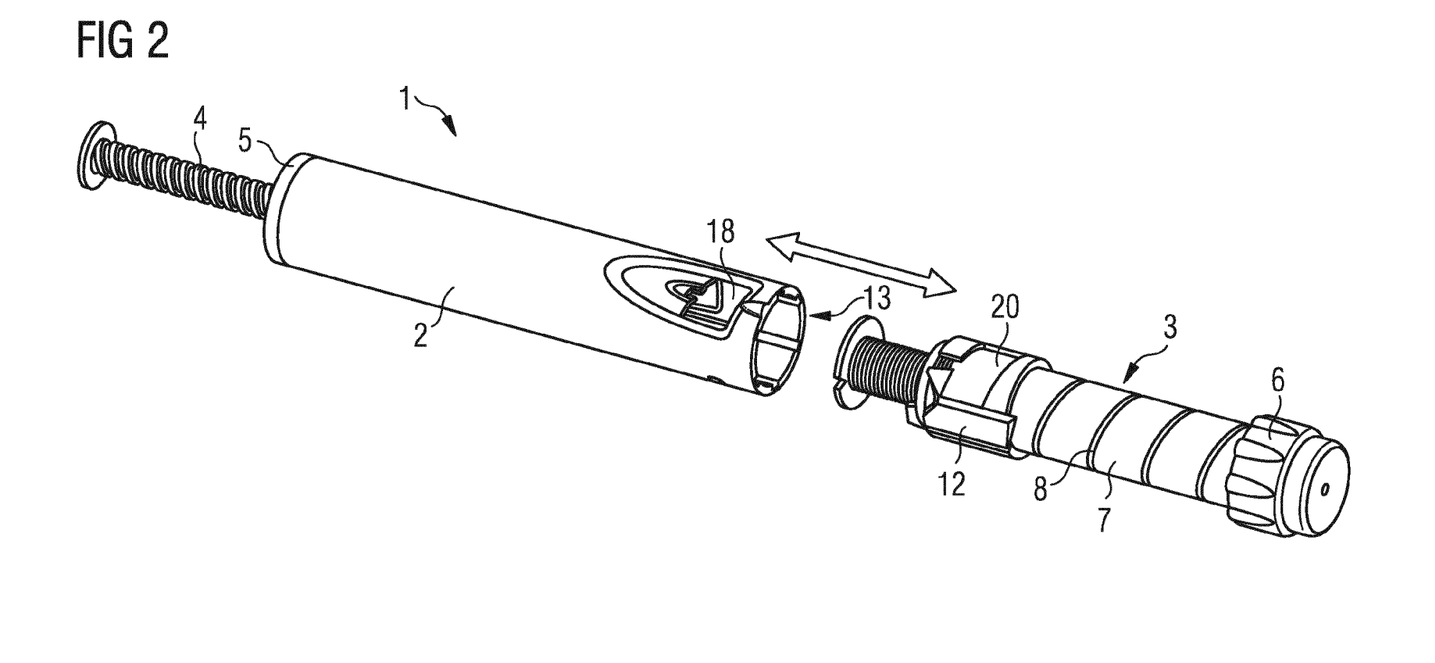
FIG. 2 shows a perspective view of the drug delivery device of FIG. 1 in a disassembled state.

The mechanical assembly 3 is retained in the housing 2 by a retaining member 12 (see FIG. 2). In particular, the retaining member 12 is engaged with the indicator member 7. The indicator member 7 comprises a thread 8 for threadedly connecting the indicator member 7 to a thread of the retaining member 12. The thread 8 of the indicator member 7 is located on an outer surface of the indicator member 7 and the thread of the retaining member 12 is located on an inner surface of the retaining member 12. Furthermore, the retaining member 12 is engaged with the housing 2, in particular with a proximal part 13 of the housing 2. The retaining member 12 is axially and rotationally fixed to the housing 2. The retaining member 12 may be a threaded insert of the housing 2.

For setting a dose, the dose setting member 6 may be rotated. Thereby, a desired size of a dose is set and/or the mechanical assembly 3 may be prepared for a subsequent dispense operation. When setting the dose, the dose setting member 6 and the indicator member 7 may move further out of the housing 2, in particular translate helically out of the housing 2. The size of the selected dose may be visible in a dose display 9. In particular, the dose display 9 may comprise an opening 18 in the housing 2 and an opening 20 of the retaining member 12 through which a part of the indicator member 7 is visible. The indication on the indicator member 7 visible in the dose display 9 may correspond to the selected dose.

When the desired dose has been set, the user may then dispense the dose by depressing a dose button 10 at the proximal end 11 of the device 1. Thereby, the indicator member 7 may move back into the housing 2 and the piston rod 4 may be advanced by the mechanical assembly 3 in a distal direction. Thereby, the piston rod 4 may drive a bung in a cartridge forwards to dispel a dose from the cartridge. Before the first use of the device 1, the piston rod 4 may be located at a start position, which may be the most proximal position of the piston rod 4 relative to the housing 2. When a dose is dispensed from the device 1, the piston rod 4 moves distally. When all doses have been dispensed from the device 1, the piston rod 4 has arrived at an end position, which may be the most distal position relative to the housing 2. Likewise, the mechanical assembly 3 or parts thereof may have a start position and an end position.

The drug delivery device 1 is a disposable device, i.e., the device 1 is meant to be disposed when the drug reservoir is empty. In other words, the drug delivery device 1 is not designed for being refilled and reused with a refilled drug. Refilling may mean exchanging an empty cartridge by a new cartridge or may mean refilling a drug in an empty cartridge. Refilling and reusing the device 1 may require a reset of the piston rod 4 and/or the mechanical assembly 3 to their respective start positions. Such a reset may only be possible when the mechanical assembly 3 or parts thereof are disassembled from the housing 2.

Although the device 1 is not designed for a removal of the mechanical assembly 3, a forceful removal may be possible by applying axial and/or bending forces to the mechanical assembly 3, in particular to the indicator member 7. As an example, when the drug reservoir is empty and the piston rod 4 has arrived at its end position, the indicator member 7 may be screwed out of the housing 2 until further proximal movement is prevented by a stop feature of the device 1. This operation may comprise a forceful overwinding of the dose setting member 6. Then, by manipulations in the region of the dose display 9, as indicated by the dotted box, mechanical forces may be transferred from the indicator member 7 to the retaining member 12 and to the housing 2. When the applied force exceeds a strength of engagement of the retaining member 12 with the indicator member 7 and/or with the housing 2, the indicator member 7 may disconnect from the housing 2. A disconnection of the indicator member 7 may result in a disconnection of the mechanical assembly 3 or further parts thereof from the housing 2. In addition to that, by the force being applied to the indicator member 7, the mechanical assembly 3 may also be disengaged from the piston rod 4. Thereby, the indicator member 7 and further parts of the mechanical assembly 3 may be forcefully disassembled from the housing 2.

FIG. 2 shows the device 1 of FIG. 1 with the mechanical assembly 3 having been forcefully removed from the housing 2. In the shown embodiment, the retaining member 12 is still engaged with the indicator member 7 and has become disengaged from the housing 2.

In order to prevent a reuse of the drug delivery device 1, the retaining member 12 is engaged with the housing 2 with high connection strength. Thereby, a forceful separation of the mechanical assembly 3 from the housing 2 is hampered. The engagement may be such that a large force is required for separating the mechanical assembly 3 from the housing 2 which may lead to visible and permanent damages in the mechanical assembly 3, the retaining member 12 and/or the housing 2. As an example, when trying to manipulate the device 1, sometimes a heating device may be used to reduce the mechanical stability of the components. Due to the high connection strength, the device 1 has to be heated for a long time and/or at a high temperature which may lead to permanent plastic deformations in the device 1. In this case, the manipulation of the device 1 may be detectable. Furthermore, due to the generated damages, a correct reassembly and/or reuse of the device 1 may be prevented.

In a further embodiment, the connection strength between the retaining member 12 and the housing 2 may be higher than the connection strength between the retaining member 12 and the mechanical assembly 3, in particular the indicator member 7. In this case, the mechanical assembly 3 will be separated from the retaining member 12 when the mechanical assembly 3 is forcefully drawn out of the housing 2. The retaining member 12 may remain in the housing 2, still being engaged with the housing 2. Such a separation of the retaining member 12 from the mechanical assembly 3, in particular from the indicator member 7, may cause severe damages in the mechanical assembly 3, in particular in the indicator member 7. As an example, cracks or deformations may be generated in the indicator member 7. The indicator member 7 may even be torn apart, such that a part of the indicator member 7 is separated from the housing and a further part of the indicator member 7 remains in the housing 2, still being engaged with the retaining member 12.

In the following, a detailed description of a retaining member 12 designed for a high connection strength with a housing 2 is described with reference to FIGS. 3A-3C, 4 and 5. In particular, this figures may be a detailed view of the retaining member 12 and the housing 2 of FIGS. 1 and 2.

Figure 3A:
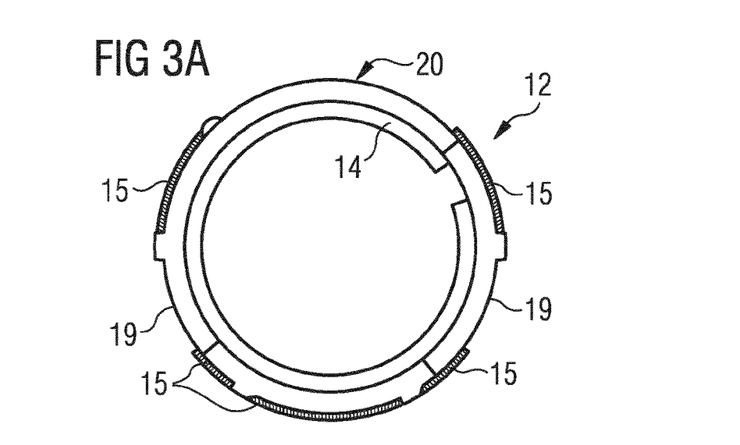
FIG. 3A shows a top view of a retaining member according to an embodiment.
Figure 3B:
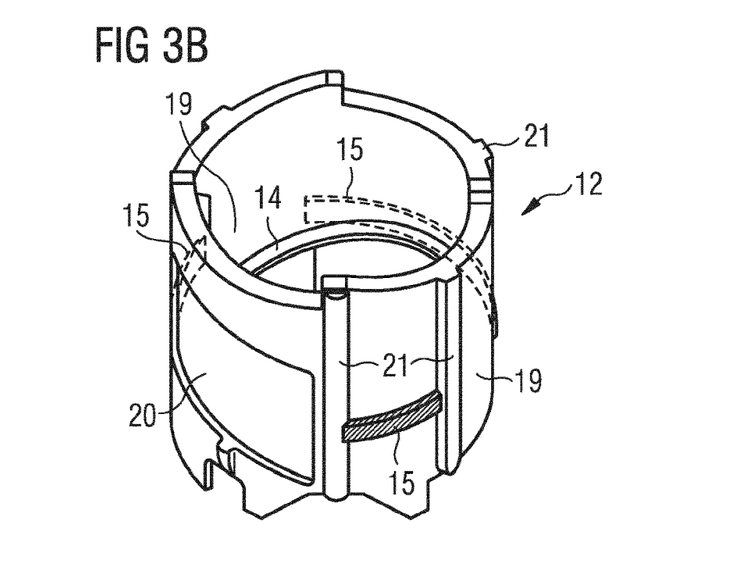
FIG. 3B shows a perspective view of the retaining member of FIG. 3A.
Figure 3C:
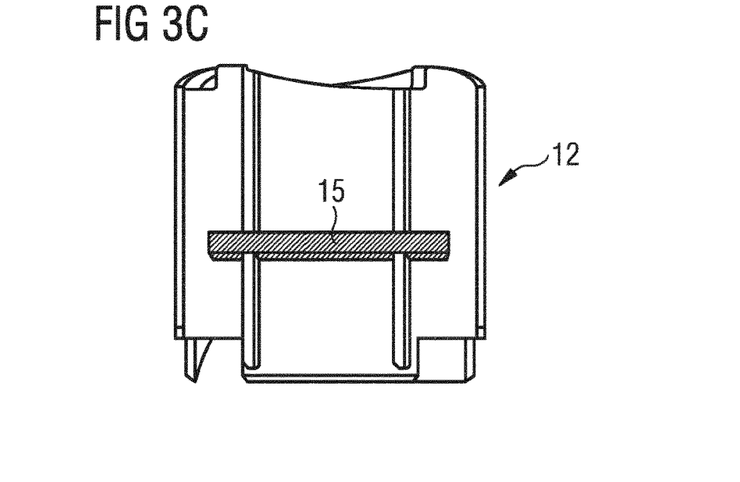
FIG. 3C shows a side view of the retaining member of FIG. 3A.
Figure 4:
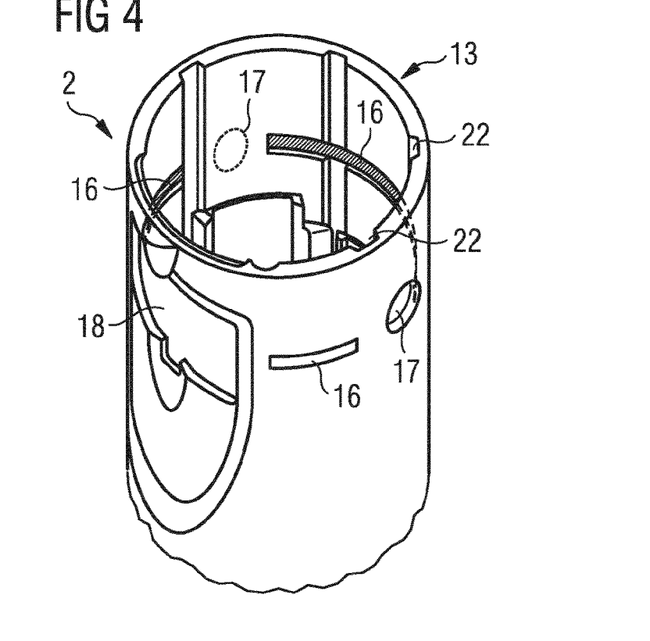
FIG. 4 shows a perspective view of a housing.
Figure 5:
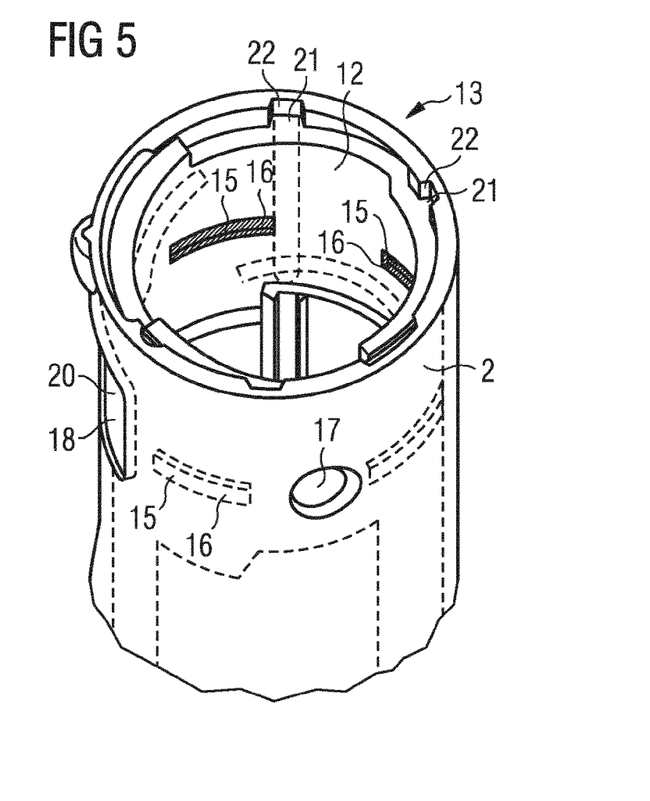
FIG. 5 shows an assembly of the retaining member of FIGS. 3A-3C with the housing of FIG. 4.

FIGS. 3A to 3C show the retaining member 12 from a top view, a perspective view and from a side view, respectively. FIG. 4 shows a detailed view of a proximal part 13 of the housing 2. FIG. 5 shows a detailed view of the retaining member 12 of FIGS. 3A to 3C when secured to the housing 2 of FIG. 4.

The retaining member 12 is designed as a nut comprising an inner thread 14 for threaded engagement with a part of the mechanical assembly 3, in particular with the indicator member 7 (see FIG. 2). The housing 2 has the shape of a sleeve. The retaining member 12 is designed to be fixed within the proximal part 13 of the housing 2. A longitudinal axis of the retaining member 12 extends through the center of the retaining member 12 into the image plane of FIG. 3A.

The retaining member 12 comprises a first engagement device 15 for engaging a second engagement device 16 of the housing 2. Preferably, the shapes of the first and second engagement devices 15, 16 enable a positive fitting of the devices 15, 16. The first engagement device 15 is designed as a ridge on an outer surface of the retaining member 12. The first engagement device 15 runs along an outer circumference of the retaining member 12. The second engagement device 16 is designed as a groove on an inner surface of the housing 2. The second engagement device 16 runs along an inner circumference of the housing 2. In alternative embodiments, the first engagement device 15 may be designed as a groove and the second engagement device 16 may be designed as a ridge. The engagement of the ridge-shaped and groove shaped engagement devices 15, 16 may be a tongue-and-groove connection. The first and second engagement device 15, 16 provide at least an axial fixation of the retaining member 12 within the housing 2. The engagement devices 15, 16 may additionally provide a rotational fixation. This strength of connection between the engagement devices 15, 16 has to be overcome when separating the retaining member 12 from the housing 2.

The first engagement device 15 and the second engagement device 16 may have an interrupted structure. Accordingly, the first and second engagement devices 15, 16 comprise several separate parts. The separate parts are located at different angular positions around the longitudinal axis of the retaining member 12 and/or the housing 2. As an example, the housing 2 may have one or more areas 17 with a reduced material thickness. The groove-shaped second engagement device 16 may not be provided in this area 17 to avoid further reducing the material thickness in this area 17. Moreover, the second engagement device 16 is interrupted by the opening 18 of the housing 2. Likewise, the first engagement device 15 is interrupted in an area 19 to be aligned with the area 17 of reduced material thickness of the housing 2 and in an opening 20 which is aligned with the opening 18 of the housing 2 for enabling a view on the indicator member 7.

Furthermore, the retaining member 12 comprises one or more first alignment members 21 for engagement with one or more second alignment members 22 of the housing 2. The first alignment members 21 may be designed as ridges running along an axial direction. The second alignment members 22 may be designed as grooves running along an axial direction. By the first and second alignment members 21, 22, a rotational alignment and/or fixation of the retaining member 12 with the housing 2 is achieved. The first and second engagement devices 15, 16 may be interrupted by the first and second alignment members 21, 22.

In order to provide a strong connection force, a direct engagement of the retaining member 12 with the housing 2 is provided along the circumference of the retaining member 12 and the housing 2. In particular, the angular range of direct engagement may be twice as large as in conventional devices. As an example, the first engagement device 15 covers in total at least half of the outer circumference of the retaining member 12. Accordingly, the first engagement device 15 covers in total at least an angular range of 180°. In other words, the interruptions of the first engagement device 15, for example by the areas 19 aligned with the areas 17 of reduced material thickness of the housing 2 and by the first alignment member 21, cover in total at most half of the circumference of the retaining member 12. Correspondingly, the second engagement device 16 of the housing covers in total at least half of the inner circumference of the housing 2. Accordingly, the second engagement device 16 covers in total at least an angular range of 180°. Thereby, direct engagement of the retaining member 12 with the housing 2 is provided in at least half of the circumference of the retaining member 12 and the housing 2. Furthermore, the radial extension of the first and second engagement devices 15, 16 are preferably selected such that a high connection strength is achieved.

The retaining member 12 and the housing 2 as shown in FIGS. 3A-3C, 4 and 5 may be produced in an injection molding process. In particular, a plastic material may be used for producing the components of the device 1. The first and second engagement devices 15, 16, in particular the ridges and grooves, may be produced by geometrically adjusting a mold core and/or a mold cavity. The exact shape of the first and second engagement devices 15, 16 may be adjusted to the desired strength of connection and/or to the specifics of the retaining member 12 and the housing 2.

REFERENCE NUMERALS 1 drug delivery device
2 housing
3 mechanical assembly
4 piston rod
5 distal end of housing
6 dose setting member
7 indicator member
8 thread
9 dose display
10 dose button
11 proximal end
12 retaining member
13 proximal part
14 thread
15 first engagement device
16 second engagement device
17 area of housing
18 opening in housing
19 area of retaining member
20 opening in retaining member
21 first alignment member
22 second alignment member

The invention claimed is:

1. A drug delivery device comprising:
   a housing;
   a mechanical assembly at least partially accommodated in the housing; and
   a retaining member for retaining the mechanical assembly in the housing, the retaining member being axially and rotationally fixed to the housing such that axial and rotational movements of the retaining member relative to the housing are prevented, wherein the retaining member is engaged with the housing, wherein a connection strength of the retaining member with the housing is larger than a connection strength of the retaining member with the mechanical assembly such that the retaining member is configured to be disengaged from the mechanical assembly when the mechanical assembly or parts thereof are forcefully separated from the housing, the disengagement of the retaining member from the mechanical assembly leading to a damage of the mechanical assembly and/or the retaining member such that the drug delivery device is configured to be damaged when the mechanical assembly or parts thereof are forcefully separated from the housing, wherein the retaining member is threadedly engaged with the mechanical assembly and comprises an inner thread for engagement with an outer thread of the mechanical assembly, wherein the mechanical assembly comprises an indicator member for displaying a size of a dose of a drug to be dispensed, and wherein the retaining member is engaged with the indicator member.

2. The drug delivery device of claim 1, wherein the retaining member is configured to prevent a reuse of the drug delivery device, wherein the disengagement of the retaining member from the mechanical assembly hampers or prevents a reassembly of the mechanical assembly with the housing of the drug delivery device.

3. The drug delivery device of claim 1, wherein:
the retaining member comprises a first engagement device, and
the housing comprises a second engagement device, and
the first and second engagement devices are configured to engage with each other.

4. The drug delivery device of claim 3, wherein the first engagement device comprises a ridge and the second engagement device comprises a groove.

5. The drug delivery device of claim 3, wherein the first engagement device extends along a circumference of the retaining member.

6. The drug delivery device of claim 3, wherein the first engagement device extends along at least half of a circumference of the retaining member.

7. The drug delivery device of claim 3, wherein the first engagement device comprises a plurality of separate parts located at different angular positions around a longitudinal axis of the retaining member.

8. The drug delivery device of claim 1, wherein the retaining member is engaged with the housing by a tongue-and-groove connection.

9. The drug delivery device of claim 1, wherein the retaining member is configured to remain in the housing when the mechanical assembly or parts thereof are forcefully separated from the housing due to the connection strength of the retaining member with the housing being larger than the connection strength of the retaining member with the mechanical assembly.

10. The drug delivery device of claim 1, wherein the drug delivery device is a pen-type injection device.

11. The drug delivery device of claim 1, further comprising a piston rod threadedly connected to the housing,
wherein the mechanical assembly is configured to drive the piston rod to expel a drug from a drug reservoir mounted in the housing.

12. The drug delivery device of claim 1, further comprising a drug reservoir containing the drug, the drug having at least one pharmaceutically active compound.

13. A retaining member for a drug delivery device, the retaining member comprising:
a first engagement device for engagement with a second engagement device of a sleeve-shaped housing of the drug delivery device to axially and rotationally fix the retaining member to the housing of the drug delivery device such that axial and rotational movements of the retaining member relative to the housing are prevented, wherein the first engagement device extends along at least half of a circumference of the retaining member, and
an alignment member configured to engage the housing of the drug delivery device to rotationally align the retaining member with the housing,
wherein the retaining member is designed to be fixed in a proximal part of the housing of the drug delivery device for retaining a mechanical assembly of the drug delivery device in the housing of the drug delivery device,
wherein the retaining member is a nut comprising an inner thread for threaded engagement with a part of the mechanical assembly.

14. The retaining member of claim 13, wherein the alignment member comprises a ridge engageable with a groove of the drug delivery device.

15. The retaining member of claim 13, wherein the first engagement device extends along a circumference of the retaining member.

16. The retaining member of claim 14, wherein the ridge extends in an axial direction.

17. The retaining member of claim 13, wherein the alignment member is one of a plurality of axially extending alignment members configured to engage the housing of the drug delivery device to rotationally align the retaining member with the housing.

* * * * *

UNITED STATES PATENT AND TRADEMARK OFFICE
CERTIFICATE OF CORRECTION

PATENT NO. : 10,869,968 B2  
APPLICATION NO. : 15/567212  
DATED : December 22, 2020  
INVENTOR(S) : Alex Meier Page 1 of 1

It is certified that error appears in the above-identified patent and that said Letters Patent is hereby corrected as shown below:

In the Specification

In Column 1, Line 10 (approx.), before "on" delete "in"

In the Claims

In Column 13, Line 35 (approx.), in Claim 3, after "device," delete "and"

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*